United States Patent [19]

Sheldon et al.

[11] Patent Number: 4,622,030
[45] Date of Patent: Nov. 11, 1986

[54] REVERSE FOLDED CONVOLUTELY WOUND TAMPON TUBE

[75] Inventors: Donald A. Sheldon; Richard R. Tews, both of Outagamie County, Wis.

[73] Assignee: Kimberly-Clark Corporation, Neenah, Wis.

[21] Appl. No.: 603,065

[22] Filed: Apr. 23, 1984

[51] Int. Cl.⁴ ............................................. A61F 13/20
[52] U.S. Cl. ...................................... 604/15; 604/11
[58] Field of Search ..................... 604/11–18

[56] References Cited

U.S. PATENT DOCUMENTS

| | | | |
|---|---|---|---|
| 3,347,234 | 10/1967 | Voss | 604/14 |
| 3,390,671 | 7/1968 | Hildebrand | 604/12 |
| 4,077,408 | 3/1978 | Murray et al. | 604/15 |
| 4,508,531 | 4/1985 | Whitehead | 604/14 |

Primary Examiner—John D. Yasko
Assistant Examiner—Sherri Vinyard
Attorney, Agent, or Firm—Paul A. Leipold; Donald L. Traut; J. J. Duggan

[57] ABSTRACT

This invention relates to a coated paper outer tube for a tube tampon providing low friction inner and outer surfaces after the tube has been formed by convolutely winding.

8 Claims, 4 Drawing Figures

REVERSE FOLDED CONVOLUTELY WOUND TAMPON TUBE

FIELD OF THE INVENTION

This invention relates to tubes for tampons and particularly convolutely wound paper tubes.

BACKGROUND OF THE INVENTION

Tampons are inserted either digitally or by insertion means which generally take the form of an outer tube which surrounds the tampon pledget and a cooperating inner tube or plunger which pushes the tampon pledget from the bottom outward through the leading edge of the outer tube.

Tampon tubes are made either of cardboard or of plastic. Plastic molding tubes are extremely expensive and comparatively difficult to manufacture because of the necessity for injection molding the outer tube. Such tubes are generally designed with bullet-shaped leading edges formed by a series of petals which must be made free of flash to prevent injury to the user during insertion. This adds further to the expense of the tube manufacture and complication inherent in the manufacturing process.

Paper tubes, on the other hand, have been found to be less aesthetically pleasing, in the past.

Convolutely wound paper tubes are preferable to spirally wound tubes because of their ease of manufacture. One of the difficulties inherent in utilizing a convolutely wound tube is that the surface on the inner portion of the tube does not have the release properties, i.e., is comparatively high friction as opposed to the visible outer surface of the outer tube. This relatively high friction inner surface makes expulsion difficult. Because of the necessity of providing an area for adherence during the convolute winding step to preserve the tubular configuration, one surface of the rectangular tube blank has been typically coated with a heat sealable thermoplastic adhesive and while only a portion of that surface is used for adhesive purposes the remainder provides a comparatively high friction surface for a tampon expulsion.

U.S. Pat. No. 2,580,665 discloses the concept of convolutely forming a paper tube with thermoplastic surfaces in contact with each other. U.S. Pat. No. 4,077,408 discloses the concept of convolutely winding for a tampon tube while the concept of convolute winding in general is explained in U.S. Pat. No. 3,252,388.

SUMMARY OF THE INVENTION

A convolutely wound tampon outer tube is provided having a low friction inner and outer surfaces for ease of insertion of the tube into the vagina as well as the ease of expulsion of the tampon pledget after insertion.

DETAILED DESCRIPTION OF THE INVENTION AND DRAWINGS

Figure 1:
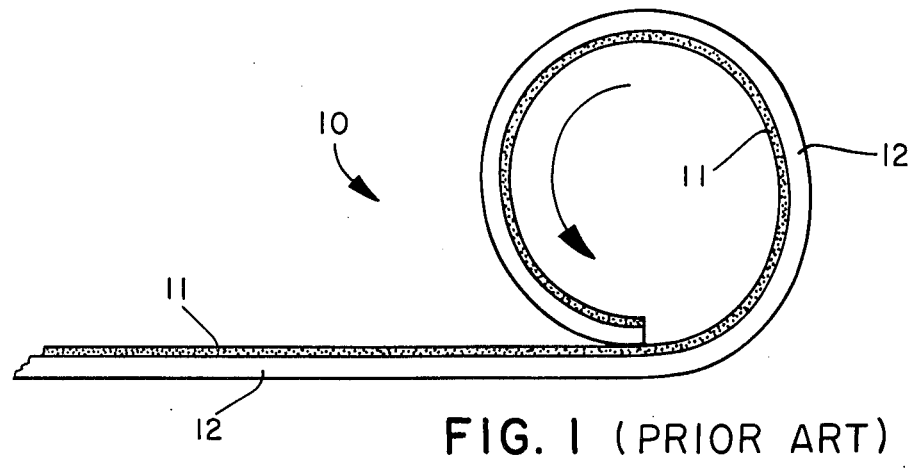
Figure 2:
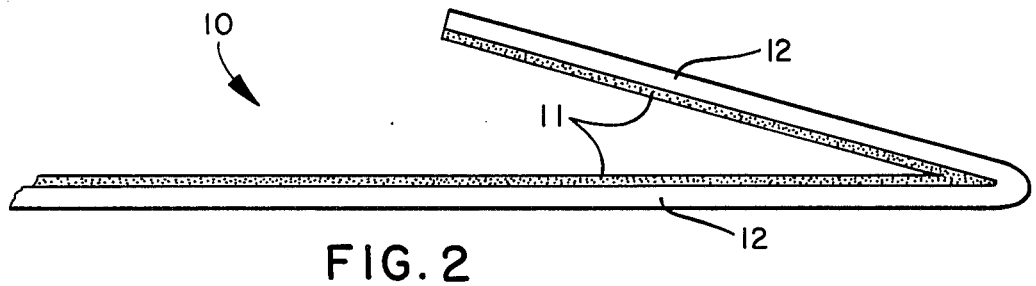
Figure 3:
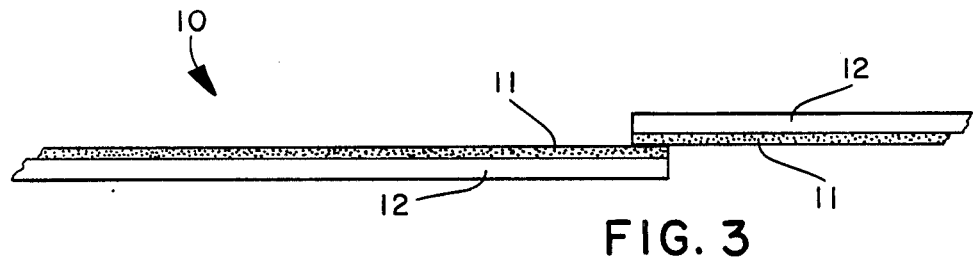
Figure 4:
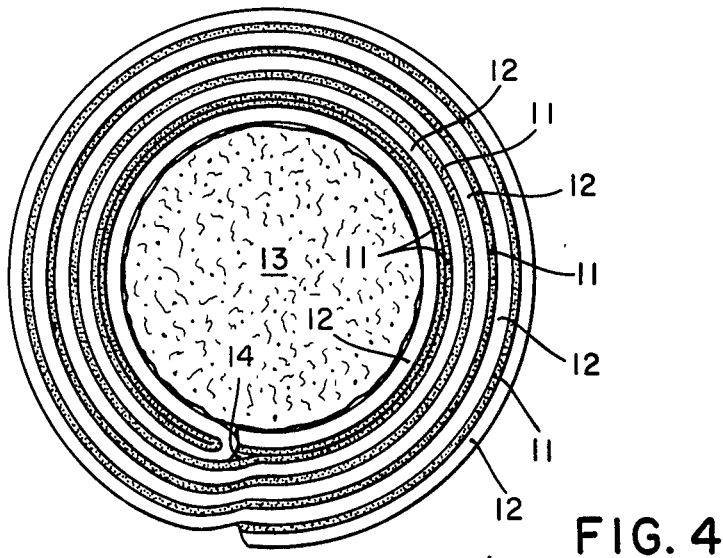

The invention may be more readily understood by reference to the drawings in which FIGS. 1, 2 and 3 are plan views of tube blanks prior to winding and FIG. 4 is a plan view of a convolutely wound tampon tube with the tampon in place.

As can be seen from FIG. 1, a rectangular tube blank 10 having high friction heat setting adhesive coating 11 and smooth surfaced coating 12 is formed in the manner taught in the prior art which consists of rolling the blank about a central axis in a conventional manner placing the high friction surface 11 on the inside and the low friction surface 12 on the outside. While this particular configuration allows for low friction insertion of the tube due to the high friction surface 11 expulsion of the tampon from the tube is difficult.

As can be seen in FIG. 2 when the rectangular tampon blank 10 is folded upon itself so that the high friction surfaces 11 are in contact with each other, when the tube is rolled, release surfaces 12 are present both on the interior and the exterior of the tube formed. In the embodiment depicted at FIG. 2, the fold occurs so that the two rectangular faces formed by the folded blank are uneven in size. The tube is wound so that the shorter rectangle is on the inner portion of the tube. The high friction portion exposed is then used for sealing purposes.

The blank depicted in FIG. 2 in a currently preferred embodiment is made by starting with an 8×3 in. wide strip of thermoplastic coated paper and folding over the first two inches. Typically, the tube is convolutely wound four times around a mandrel which is preferably 0.64 inches in diameter, although winding need only be twice around the mandrel to accomplish the desired surface configuration.

FIG. 3 shows an alternative method of configuring of the tube blank prior to winding which two separate rectangular portions are joined so that an edge of the high friction surface 11 of 1 abutts the high friction surface of the other. These surfaces are then overlap sealed to provide suitable configurations for convolutely winding. The overlap seal need not be more than about ⅜ of an inch in the transverse direction.

The tube formed from the blank according to FIGS. 2 and is depicted in FIG. 4 with the tampon 13 shown in place and the overlap seal 14 used to maintain the configuration of the tube.

The use of a heat-setting thermoplastic adhesive as the high friction surface is only one way of obtaining sealing of the tampon tube. It is possible according to the teachings of this invention to merely use a narrow band of a pressure sensitive adhesive applied to the high friction surface which would be activated during the convolute winding and formation of the tube itself. Any number of alternative adhesive means will also suggest themselves to those with skill in the art and are within the ambit of this invention. Any adhesive configuration or combination which seals the folded or overlapped wound tubes in a manner providing a low friction inner and outer surface is contemplated by this invention.

We claim:

1. A convolutely wound cellulosic outer tampon tube said tube comprising a low-friction inner surface and a low-friction outer surface and adhesive bonding means to maintain said tubular configuration wherein said tube is wound from a blank having a low-friction surface and an adhesive-coated nonlow-friction surface said adhesive-coated surface is folded upon itself at one end of said blank prior to winding said tube with said adhesive-coated faces in face-to-face contact in the fold to create an area that forms a low-friction inner surface after winding.

2. Method for making convolutely wound tampon tubes said tube having a low-friction inner and outer surface said method comprising:
 (a) transversely folding one end of a rectangular faced tampon blank having a low-friction face and non-low-friction adhesive-coated face upon itself with said nonlow-friction face on the inner side of said fold, with said low-friction face forming the outer faces resulting from said fold, each of said outer faces being rectangular;

(b) convolutely winding said folded blank to form a tube with a low-friction outer surface and a low-friction inner surface, wherein the folded portion forms the inner surface of said tube and the adhesive coating on the nonlow-friction face seals the convolutely wound blank to form the tube.

3. The method of claim 2 wherein one of the rectangles formed by folding is larger than the other and adhesive attachment means are present on the non-low friction face of the larger rectangle which extends beyond the smaller rectangle.

4. A tampon comprising in combination a cylindroidal pledget and as a convolutely wound cellulosic outer tampon tube said tube comprising a low-friction inner surface and a low-friction outer surface and adhesive bonding means to main said tubular configuration wherein said tube is wound from a blank having a low-friction surface and a non-low-friction adhesive-coated surface said adhesive-coated surface is folded upon itself at one end of said blank prior to winding said tube with said adhesive-coated faces in face-to-face contact in the fold to create an area that forms a low-friction inner surface after winding.

5. The method of claim 2 wherein said folded portion corresponds in length to the inner circumference of said tube.

6. The method of claim 2 wherein said nonlow-friction adhesive-coated face comprises a heat-setting thermoplastic adhesive.

7. The method of claim 2 wherein the convolute winding comprises winding at least twice around a mandrel.

8. A method for making of convolutely wound tampon tube having a low-friction inner and low-friction outer surface comprising:

providing two blanks each having a nonlow-friction adhesive-coated face and a low-friction face, overlapping said blanks such that said nonlow-friction faces are in adhesive contact, convolutely winding the adhesively connected blanks to form a tube such that said low-friction faces of said blanks are on both the inner and outer surfaces of the tube, sealing said wound blanks to form said tampon tube.

* * * * *